United States Patent [19]
Hall et al.

[11] Patent Number: 5,612,778
[45] Date of Patent: Mar. 18, 1997

[54] FIBER OPTIC SENSOR FOR MULTIPLE VARIABLES

[75] Inventors: Christopher J. Hall, Satellite Beach; Calvin L. Adkins, Palm Bay, both of Fla.; David Graves, Lawrenceville, Ga.; Ed Bryant, Fellsmere, Fla.

[73] Assignee: Harris Corp., Melbourne, Fla.

[21] Appl. No.: 544,704

[22] Filed: Oct. 18, 1995

[51] Int. Cl.$^6$ .............................. G01C 3/08; G02B 27/00
[52] U.S. Cl. ...................... 356/4.09; 356/345; 359/577
[58] Field of Search .................... 356/4.09, 345; 359/577

[56] References Cited

U.S. PATENT DOCUMENTS

| | | | |
|---|---|---|---|
| 5,301,001 | 4/1994 | Murphy et al. | 356/35.5 |
| 5,359,405 | 10/1994 | Andrews | 356/35.5 |
| 5,361,130 | 11/1994 | Kersey et al. | 356/345 |
| 5,380,995 | 1/1995 | Udd et al. | 250/227.18 |
| 5,488,475 | 1/1996 | Friebele et al. | 356/352 |

*Primary Examiner*—Mark Hellner
*Attorney, Agent, or Firm*—Rogers & Killeen

[57] ABSTRACT

An optical device and method for sensing a plurality of ambient conditions (e.g., temperature and pressure) may include transmission of an optical flux through a fiber optic cable to a section of the cable that is placed where the ambient conditions are to be sensed. The section of cable includes a plurality of serially aligned sensors for reflecting the optical flux back through the cable, each of the sensors having semi-reflective surfaces at the two ends thereof for partially reflecting the optical flux. The distance between the two ends of each sensor varies primarily as a function of a different one of the ambient conditions. The optical flux is partially transmitted and partially reflected at each of the ends of the sensors and the optical flux reflected back through the cable includes an interference pattern that is a function of each sensor's end-to-end distance. A detector evaluates the interference pattern to determine the ambient conditions. The evaluation of the interference pattern may be simplified by properly selecting the reflectivity of the ends of the sensors.

17 Claims, 1 Drawing Sheet 5,612,778

FIBER OPTIC SENSOR FOR MULTIPLE VARIABLES

BACKGROUND OF THE INVENTION

The present invention relates to fiber optic sensors, and more specifically to a fiber optic sensor and method in which plural ambient conditions are determined.

Fiber optic systems for sensing ambient conditions at otherwise inaccessible locations are known. For example, fiber optic sensors may be used to monitor blood pressure inside a blood vessel. In such systems, as shown by way of example in FIG. 1, a fiber optic cable 12 is provided with a sensor 14 at a remote end that is placed where the blood pressure is to be measured. A source of light 16, such as a light emitting diode (LED), transmits a light signal through the cable 12 to the sensor 14 at the remote end. The sensor 14 may include two semi-reflective surfaces 18 and 20 that are spaced from each other by a distance D1 that varies as a function of the pressure on the sensor 14. The surface 18 partially reflects and partially transmits the received light signal, while the surface 20 reflects the light transmitted through the surface 18. The partially reflected light from the surface 18 and reflected light from surface 20 cause an interference pattern to form in the cable 12. The intensity of the light in the cable will vary as the distance between the two surfaces changes in response to blood pressure changes. The intensity may be sensed to thereby indicate changes in blood pressure. See, for example, U.S. Pat. No. 4,709,413 issued Nov. 24, 1987 to Forrest, et al.

There are several problems with such systems that limit their usefulness. First, they are only able to measure one condition. If the changes in a second condition, such as temperature, are also desired, a second cable with a separate sensor must be provided. A second cable increases complexity and cost, and more importantly it may not be possible to insert a second cable in a narrow channel. Further, sensors for measuring one condition such as pressure are typically also sensitive to another condition such as temperature so that they do not give an accurate reading of pressure if temperature changes.

Accordingly, it is an object of the present invention to provide a novel optical sensing method and device that obviates the problems of the prior art.

It is another object of the present invention to provide a novel optical sensing method and device in which plural ambient conditions are measured with a single optical fiber.

It is yet another object of the present invention to provide a novel optical sensing method and device in which plural serially aligned sensors at the end of a single optical fiber sense different ambient conditions.

It is still another object of the present invention to provide a novel optical sensing method and device in which plural serially aligned sensors at the end of a single optical fiber partially reflect and partially transmit an optical signal to form an interference pattern in the optical fiber.

It is a further object of the present invention to provide a novel optical sensing method and device in which plural serially aligned sensors at the end of a single optical fiber form an interference pattern in the fiber that is a function of each of the ambient conditions separately sensed by the plural sensors.

It is yet a further object of the present invention to provide a novel method and device for remotely sensing plural ambient conditions in which plural serially aligned sensors in an optical fiber include semi-reflective ends for reflecting an optical signal to form an interference pattern in the optical fiber that is a function of the distances between the semi-reflective ends of each sensor.

It is still a further object of the present invention to provide a novel method and device for remotely sensing plural ambient conditions in which plural serially aligned sensors in an optical fiber include semi-reflective ends for reflecting an optical signal to form an interference pattern and in which the reflectivities of each sensors' ends are chosen to simplify the evaluation of the ambient conditions.

These and many other objects and advantages of the present invention will be readily apparent to one skilled in the art to which the invention pertains from a perusal of the claims, the appended drawings, and the following detailed description of the preferred embodiments.

DESCRIPTION OF PREFERRED EMBODIMENTS

Figure 1:
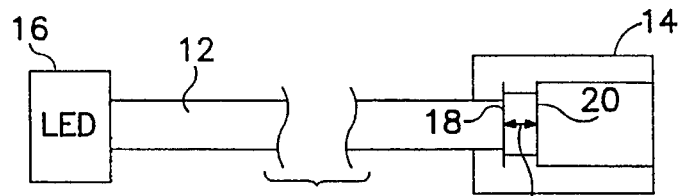
FIG. 1 is schematic diagram of an optical sensing system of the prior art.
Figure 2:
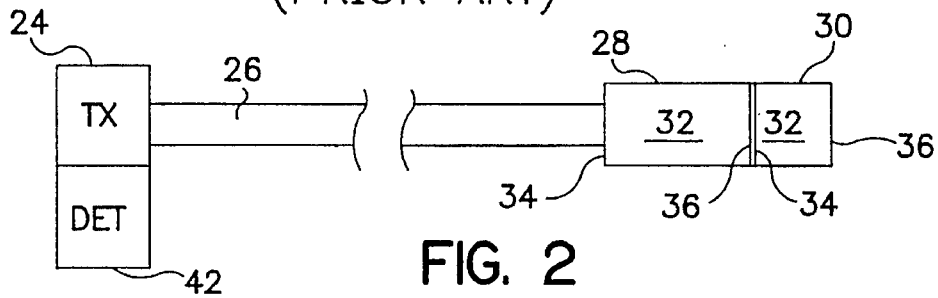
FIG. 2 is schematic diagram of an optical sensing system of the present invention.

With reference now to FIG. 2, an embodiment 22 of the present invention may include a conventional optical signal transmitter 24 for transmitting a continuous wave optical flux through an optical cable 26 to a pair of sensors 28 and 30 at a section of the cable 26 that is to be placed where conditions are to be sensed. Each of sensors 28 and 30 may include a core 32 between two ends 34 and 36. The length of core 32 may be responsive to a particular condition, such as temperature, pressure, relative humidity, energy field intensity, velocity of surrounding fluid (which causes the fiber to stretch), etc. As the length of core 32 changes, the distance between ends 34 and 36 also changes. As will be appreciated, each core 32 may respond primarily to one condition, but may be affected by the other sensed condition. Desirably, the responses of cores 32 are independent of each other, although some dependence is acceptable.

For example, where:

Optical length of sensor 28=F(pressure, temperature)

Optical length of sensor 30=G(temperature, pressure)

F( ) and G( ) are desirably as independent as reasonably possible, and each is desirably predominantly affected by a different condition.

Cores 32 of sensors 28 and 30 may comprise material appropriate for the condition to be sensed. For example, a conventional single mode optical fiber may be tailored using known processes to have the specific characteristics for sensing the various properties. Core 32 of one of the sensors may be a portion of the optical cable partitioned by the semi-reflective ends 34 and 36. Sensors 28 and 30 are desirably the same diameter as cable 26, or may be slightly larger depending on the application. Sensors 28 and 30 may be joined to each other and to cable 26 conventionally, such as by using silicon V-groove technology that is used to align and secure fibers, or by using other methods known in the art.

Figure 3:
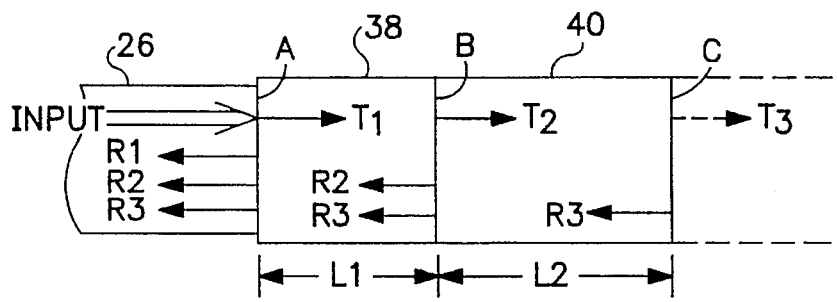
FIG. 3 is pictorial representation of sensors of the present invention illustrating reflection of the optical flux.

Each of ends 34 and 36 may include a semi-reflective surface for partially reflecting and partially transmitting optical signals transmitted through cable 26. By way of example, and with reference to FIG. 3, two sensors 38 and 40 of lengths L1 and L2 may have semi-reflective surfaces A, B, and C at their ends. Length L1 of sensor 38 may be predominantly affected by a first condition and length L2 of sensor 40 may be predominantly affected by a second condition. A continuous wave optical flux arriving at surface A may be partially transmitted as indicated by arrow T1 and partially reflected as indicated by arrow R1. The transmitted portion T1 passes through core 32 of sensor 38 to surface B where it is partially transmitted T2 and partially reflected R2. The transmitted portion T2 passes through core 32 of sensor 40 to surface C where it may be reflected R3. The combination of R1, R2 and R3 with the incoming continuous wave optical flux creates an interference pattern in the optical cable. If additional sensors or a further length of optic fiber is attached to sensor 40, surface C may partially transmit a portion T3 to the further sensor or fiber.

The length of fiber optic cable 26 is not a factor in the sensing method herein (cable length will, of course, be affected by factors such as attenuation, power of the light source, dynamic range of the detector, etc.) because all of the sensing is performed in sensors 28 and 30. Sensors 28 and 30 may be at the end of a cable 26, or at an intermediate point.

With reference again to FIG. 2, the interference pattern in cable 26 may be detected by a conventional photo-detector 42. The detected optical signal may be converted to an electrical signal for processing. As will be explained below, the processor solves two equations with two unknowns to determine how the length of each sensor is affected by the condition it senses, and may provide an absolute value of the condition. Detector 42 senses relative brightness and calibration may be needed to obtain absolute values of the sensed conditions. For example, detector 42 may be calibrated for known values of the sensed conditions before use. The processor can provide an indication of condition change without calibration.

In another embodiment, the semi-reflective surfaces at the ends of each sensor may be polarization gratings. For example, and with reference again to FIG. 3, surface A may be partially reflective to vertical polarization, and be arranged to pass horizontal light with essentially no loss. Surface B may be a polarization independent semi-reflector, and surface C may be partially reflective to horizontal polarization and pass as much vertical polarization as possible to prevent cross-coupling of the sensors. In this embodiment the input optical flux may be dual-polarized (or have two spectral lines) and detector 42 for the reflected optical signal would include two detectors with appropriate polarization (or spectral separation).

Alternatively, the semi-reflective surfaces may be dichroic mirrors (dielectrics) and the optical flux may be provided in two wavelengths. Transmitter 24 may transmit an unpolarized optical flux, and detector 42 may include a Fast Fourier Transform for evaluating the received interference pattern.

Figure 4:
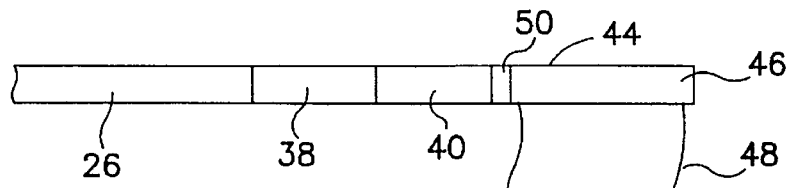
FIG. 4 is a pictorial representation of a further embodiment of the present invention.

In yet another embodiment, additional sensors may be provided for sensing further conditions. For example, and with reference to FIG. 4, a third sensor 44 may include a core with surface metalization 46 that is heated responsive to a current therethrough. The heat would affect the core length of third sensor 44 and the change of length may be determined in the manner discussed above. The current may be provided by connecting the metalized portion 46 to a circuit 48 that senses an induced current as illustrated, or metalized portion 46 may be unconnected to any other circuit and placed in an energy field. In either event third sensor 44 is heated and the measured temperature may be used to indicate a current through a wire or a field intensity. A metalized third sensor 44 that is not electrically connected may be used to advantage to probe an energy field without disturbing the field as may be done by introduction of conventional electrically connected probes. Metalization 46 may be separated from the other sensors by a spacer 50 to protect the other sensors from the heat.

By way of further explanation, the theoretical basis for the present invention may be more clearly understood with reference to the following example.

Optical fiber can be used to sense pressure and temperature because the optical path length is sensitive to these parameters. However both parameters affect the fiber in the same way (by changing the optical path length) and there has been no way to decouple the effects of the two conditions with a single sensor.

Figure 5:
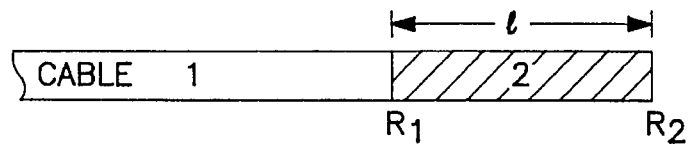
FIG. 5 is pictorial representation of a single etalon of the prior art.

With reference to FIG. 5, a single sensor of the prior art may comprise an etalon 2 defined as a length 1 of sensor between two mirrors $R_1$ and $R_2$ on the end of a fiber 1. As is known, it is possible to monitor variations in the optical path length 1.

The coherent interference of multiple path beams produces a total amplitude (reflected or transmitted):

$$A_T = [1 - r_1 r_2 e^{i\theta}]^{-1} \quad (1)$$

where $$\theta = \frac{2nl}{\lambda}$$

and $r_i$ is amplitude reflection.

The total intensity is:

$$I_T = A_T A_T^* = [1 + r_1^2 r_2^2 - (r_1 + r_2)\cos\theta]^{-1} \quad (2)$$

By measuring the phase change, $\Delta\theta$, the optical path length change, $\Delta$, is calculated as:

$$\Delta = 2n\Delta l = \Delta\theta \frac{(\lambda)}{2\pi} \quad (3)$$

$\Delta$ is a function of temperature and pressure as follows:

$$\Delta = \Delta T \frac{d}{dT}(2nl) + \Delta P \frac{d}{dP}(2nl) \quad (4)$$

$$\Delta = \Delta T \left(2n\frac{dl}{dT} + 2l\frac{dn}{dT}\right) + \Delta P \left(2n\frac{dl}{dP} + 2l\frac{dn}{dP}\right) \quad (5)$$

$$\Delta = \Delta T(A_T + B_T) + \Delta P(A_P + B_P) \quad (6)$$

where $A_T$, $B_T$, $A_p$, $B_p$ are material constants and $\Delta T$, $\Delta P$ are variables acting on the fiber.

Thus there is but one measurement $\Delta$ and two variables, $\Delta T$ $\Delta P$ that cannot be decoupled to provide an indication of the separate affect of each.

It would, of course, be possible to use two separate probes, each with a different sensor. If we use two separate etalons with different material constants then $$\Delta_1 = \Delta T(A_{T1} + B_{T1}) + \Delta P(A_{P1} + B_{P1}) \quad (7)$$

$$\Delta_2 = \Delta T(A_{T2} + B_{T2}) + \Delta P(A_{P2} + B_{P2}) \quad (8)$$

giving us two measurements $\Delta_1$, $\Delta_2$ and two variables $\Delta T$, $\Delta P$ which can be solved to decouple the effects of each.

$$\Delta P = \frac{\Delta_1(A_{T2}+B_{T2})-\Delta_2(A_{T1}+B_{T1})}{(A_{P1}+B_{P1})(A_{T2}-B_{T2})-(A_{P2}-B_{P2})(A_{T1}-B_{T1})} \quad (9)$$

$$\Delta T = \frac{\Delta_1(A_{P2}+B_{P2})-\Delta_2(A_{P1}+B_{P1})}{(A_{P2}+B_{P2})(A_{T1}-B_{T1})-(A_{P1}-B_{P1})(A_{T2}-B_{T2})} \quad (10)$$

Figure 6:
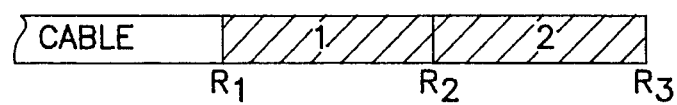
FIG. 6 is pictorial representation of a double etalon of the present invention.

In an embodiment of the present invention, the amplitude reflections $r_i$ are properly selected so that some of the terms in the intensity equation may be dropped and so that changes in conditions may be determined as if two separate probes were being used. With reference now to FIG. 6, a single fiber may have two etalons 1 and 2 back-to-back separated by mirrors $R_1$, $R_2$, and $R_3$. Similar to the single etalon, the total amplitude of two back-to-back etalons (coherently coupled) is:

$$A_T = [1 - r_1 r_2 e^{i\theta_1} - r_2 r_3 e^{i\theta_2} - R_1 r_3 e^{i(\theta_1+\theta_2)}]^{-1} \quad (11)$$

The intensity is:

$$I_T = [(1 - r_1 r_2 e^{i\theta_1} - r_2 r_3 e^{i\theta_2} - r_1 r_3 e^{i(\theta_1+\theta_2)}) \quad (12)$$
$$(1 - r_1 r_2 e^{-i\theta_1} - r_2 r_3 e^{-i\theta_2} - r_1 r_3 e^{-i(\theta_1+\theta_2)})]^{-1}$$

where $$\theta_1 = \frac{2nl_1}{\lambda} \rightarrow \text{etalon (1)} \quad (13)$$

$$\theta_2 = \frac{2nl_2}{\lambda} \rightarrow \text{etalon (2)} \quad (14)$$

$$\theta_1 + \theta_2 = \frac{2n(l_1+l_2)}{\lambda} \rightarrow \quad (15)$$

The intensity may be rewritten as:

$$I_T = [A + B\cos\theta_1 + C\cos\theta_2 + D\cos(\theta_1-\theta_2) + E\cos(\theta_1+\theta_2)]^{-1} \quad (16)$$

where $$A = 1 + (r_1 r_2)^2 + (r_1 r_3)^2 + (r_2 r_3)^2 \quad (17)$$

$$B = 2(r_1 r_2 r_3 - r_1 r_2) \quad (18)$$

$$C = 2(r_1^2 r_2 r_3 - r_2 r_3) \quad (19)$$

$$D = 2r_1 r_2^2 r_3 \quad (20)$$

$$E = -2r_1 r_3 \quad (21)$$

Some of the coefficients may be simplified or reduced to zero by selecting proper values of $r_1$, $r_2$ and $r_3$. For example:

$r_1 = 0.1$    $A = 1.05$
$r_2 = 0.2$    $B = 0$
$r_3 = 1.0$    $C = -0.396$
             $D = 0.008 \approx 0$
             $E = -0.2$ and Equation (12) becomes:

$$I_T \approx [A + C\cos\theta_2 + E\cos(\theta_1+\theta_2)]^{-1} \quad (22)$$

and $$\Delta_1 = \theta_2 \frac{(\lambda)}{2\pi} \quad \Delta_2 = (\theta_1+\theta_2)\frac{\lambda}{2\pi} - \theta_2\frac{(\lambda)}{2\pi} \quad (23)$$

Thus, values of $\Delta_1$ and $\Delta_2$ are obtained that may be used in Equations (9) and (10) to obtain $\Delta P$ and $\Delta T$ as if the sensors were decoupled.

This analysis can be extended to N variables using N etalons to measure N values of $\Delta$. The N variables can be solved for in terms of material parameters and measurements $\Delta_1$, $\Delta_2$, ... $\Delta_N$.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. An optical device for sensing plural ambient conditions comprising:

a transmitter for transmitting a continuous wave optical flux through a fiber optic cable to a section of said cable that is for placement where plural ambient conditions are to be sensed;

plural serially aligned sensors at said section of said cable for reflecting the optical flux back through said cable, each of said sensors having semi-reflective surfaces at ends thereof for partially reflecting the optical flux and a core between said two ends with a length that varies primarily as a function of a different one of the plural ambient conditions, wherein the optical flux is partially transmitted and partially reflected at each of said ends of said sensors and the optical flux reflected back through said cable includes an interference pattern that is a function of the length of each said core; and a detector for receiving the reflected optical flux and for evaluating the interference pattern to evaluate the ambient conditions sensed by said sensors.

2. The device of claim 1 wherein said transmitter transmits an unpolarized optical flux, and said detector comprises a Fast Fourier Transform means for evaluating the interference pattern.

3. The device of claim 1 wherein said section of said cable is at an end of said cable.

4. The device of claim 1 wherein the ambient conditions are selected from pressure, temperature, speed, relative humidity, and energy field intensity.

5. The device of claim 1 wherein said transmitter transmits a plural-polarized optical flux, and wherein said semi-reflective ends of one of said sensors are of different polarization than said semi-reflective ends of another of said sensors, whereby the reflected optical flux includes plural polarizations.

6. The device of claim 5 wherein said detector separately detects the plural polarizations of the reflected optical flux.

7. A method of sensing plural ambient conditions comprising the steps of:

(a) providing a fiber optic cable with plural serially aligned sensors at a section of the cable, each of the sensors having semi-reflective surfaces at two ends thereof for partially reflecting and partially transmitting an optical flux transmitted to the remote end of the cable and a distance between the two ends that varies primarily as a function of a different one of the plural ambient conditions;

(b) placing the section of the fiber optic cable where the plural ambient conditions are to be sensed;

(c) transmitting a continuous wave optical flux through the fiber optic cable to the section of the cable;

(d) partially transmitting and partially reflecting the optical flux at each of the semi-reflective ends of the sensors so that the optical flux reflected back through the cable includes an interference pattern that is a function of the distance between the two ends of each of the sensors; and (e) evaluating the received interference pattern to determine the sensed ambient conditions.

8. The method of claim 7 further comprising the step of calibrating a received interference pattern for known ambient conditions, whereby the method provides absolute values of the sensed ambient conditions.

9. The method of claim 7 wherein the optical flux is unpolarized and the step of evaluating the interference pattern includes evaluation of a Fast Fourier Transform.

10. The method of claim 7 wherein there are two sensors at the remote end of the cable and the sensed ambient conditions are temperature and pressure, and further comprising the step of dual-polarizing the optical flux.

11. The method of claim 7 wherein the step of evaluating the received interference pattern comprises the step of selecting the semi-reflective ends so that amplitudes of reflections from the ends allow the evaluation of the received interference pattern to proceed as if the sensors were independent.

12. An optical device for sensing plural ambient conditions comprising:

a fiber optic cable for receiving an optical flux; and plural serially aligned sensors at a portion of said cable where the plural ambient conditions are to be sensed for reflecting the optical flux back through said cable, each of said sensors having semi-reflective surfaces at ends thereof for partially reflecting the optical flux, and each of said sensors comprising a core between said two ends of a different material so that a length of said core varies primarily as a function of a different one of the plural ambient conditions for each of said sensors, wherein the optical flux is partially transmitted and partially reflected at each of said ends of said sensors and the optical flux reflected back through said cable includes an interference pattern that is a function of the length of each said core.

13. The device of claim 12 wherein the optical flux is unpolarized.

14. The device of claim 13 wherein the optical flux is plural-polarized, and wherein said semi-reflective ends of one of said sensors are of different polarization than said semi-reflective ends of another of said sensors, whereby the reflected optical flux includes plural polarizations.

15. The device of claim 13 wherein each of said sensors is responsive to a different one of the plural ambient conditions selected from the group consisting of pressure, temperature, speed, relative humidity, and energy field intensity.

16. The device of claim 13 wherein one said core further comprises a metallic portion for sensing a field intensity.

17. The device of claim 1 wherein one said core further comprises a metallic portion for sensing a field intensity.

* * * * *